US011033234B2

(12) United States Patent
Wong et al.

(10) Patent No.: US 11,033,234 B2
(45) Date of Patent: Jun. 15, 2021

(54) OPTICAL IMAGING SYSTEM AND METHOD OF MAKING AND USING THE SAME

(71) Applicant: THE JOHNS HOPKINS UNIVERSITY, Baltimore, MD (US)

(72) Inventors: John Wong, Towson, MD (US); Ken Kang-Hsin Wang, Laurel, MD (US); Iulian Ioan Iordachita, Lutherville, MD (US)

(73) Assignee: The Johns Hopkins University, Baltimore, MD (US)

( * ) Notice: Subject to any disclaimer, the term of this patent is extended or adjusted under 35 U.S.C. 154(b) by 1056 days.

(21) Appl. No.: 15/520,973

(22) PCT Filed: Oct. 22, 2015

(86) PCT No.: PCT/US2015/056866
§ 371 (c)(1),
(2) Date: Apr. 21, 2017

(87) PCT Pub. No.: WO2016/065121
PCT Pub. Date: Apr. 28, 2016

(65) Prior Publication Data
US 2018/0020985 A1    Jan. 25, 2018

Related U.S. Application Data

(60) Provisional application No. 62/067,340, filed on Oct. 22, 2014.

(51) Int. Cl.
*A61B 5/00*      (2006.01)
*A61B 50/13*     (2016.01)
*A61B 6/03*      (2006.01)

(52) U.S. Cl.
CPC ............ *A61B 5/704* (2013.01); *A61B 5/0064* (2013.01); *A61B 5/0071* (2013.01);
(Continued)

(58) Field of Classification Search
None
See application file for complete search history.

(56) References Cited

U.S. PATENT DOCUMENTS 7,190,991 B2 *  3/2007  Cable ................... A61B 5/0059
                                                600/407
8,050,735 B2   11/2011  Feke et al.
(Continued)

OTHER PUBLICATIONS

Tuli et al. "Accuracy of Off-Line Bioluminescence Imaging to Localize Targets in Preclinical Radiation Research." Radiation Research. Apr. 2013 179(4): 416-421. (Year: 2013).*
Eslami et al. "An Integrated X-Ray-Optical Tomography System for Pre-clinical Radiation Research." Proc SPIE Mar. 6, 2013; 8668: 866830-(Year: 2013).*
(Continued)

*Primary Examiner* — Luther Behringer
(74) *Attorney, Agent, or Firm* — Johns Hopkins Technology Ventures

(57) ABSTRACT

An optical imaging system for interfacing with a separate examination apparatus and methods of making and using the same are disclosed. The optical imaging system can include an imaging housing including a housing enclosure and a housing receptor plate, a subject support mount, a cart including an extendable arm, an optical arrangement including an optical source, a cantilever mirror system, and the housing enclosure, and a detection optical path providing optical communication between the cantilever mirror system and an optical detector. The subject support mount allows optical illumination via at least one optical port. The extendable arm is affixed to the cart at one end and the optical arrangement at another end. The extendable arm can move from a retracted position to an extended position without contacting the subject support mount or the subject.

15 Claims, 3 Drawing Sheets

(52) U.S. Cl.
CPC .......... *A61B 5/0073* (2013.01); *A61B 5/0077* (2013.01); *A61B 5/0079* (2013.01); *A61B 50/13* (2016.02); *A61B 5/0035* (2013.01); *A61B 6/032* (2013.01); *A61B 2503/40* (2013.01)

(56) References Cited

U.S. PATENT DOCUMENTS

| | | | |
|---|---|---|---|
| 8,078,256 B2 * | 12/2011 | Zan | A61B 6/44 600/415 |
| 8,175,220 B2 | 5/2012 | Vaisburd et al. | |
| 2014/0267697 A1 | 9/2014 | Wong et al. | |
| 2015/0012224 A1 | 1/2015 | Klose et al. | |

OTHER PUBLICATIONS

Yang et al. "Systematic calibration of an integrated x-ray and optical tomography system for preclinical radiation research." Med. Phys. 42 (4), Apr. 2015 (Year: 2015).*

Dehghani, et al., Near infrared optical tomography using NIRFAST: Algorithm for numerical model and image reconstruction. Commun Numer Methods Eng 2008, 25(6), 711-732.

Jermyn, et al., Fast segmentation and high-quality three-dimensional volume mesh creation from medical images for diffuse optical tomography. J Biomed Opt 2013, 18(8), 86007.

He, et al., Sparse reconstruction for quantitative bioluminescence tomography based on the incomplete variables truncated conjugate gradient method. Opt Express 2010, 18(24), 24825-24841.

Cunha, et al., Preclinical imaging: an essential ally in modern biosciences. Mol Diagn Ther 2014, 18(2), 153-73.

* cited by examiner

OPTICAL IMAGING SYSTEM AND METHOD OF MAKING AND USING THE SAME

CROSS-REFERENCE TO RELATED APPLICATIONS

This application is a 35 U.S.C. § 371 U.S. national entry of International Application PCT/US2015/056866, having an international filing date of Oct. 22, 2015, which claims the benefit of U.S. Provisional Application No. 62/067,340, filed Oct. 22, 2014, the content of each of the aforementioned applications is herein incorporated by reference in their entirety.

STATEMENT REGARDING FEDERALLY SPONSORED RESEARCH

This invention was made with government support under R01-CA158100 awarded by the National Institutes of Health. The government has certain rights in the invention.

BACKGROUND OF THE INVENTION

The field of the disclosure is optical imaging systems. More particularly, the disclosure relates to a dual-use optical tomographic imaging system for pre-clinical research as an independent instrument or on-board other instruments.

Molecular optical imaging, including both bioluminescence and fluorescence imaging, is an important modality for pre-clinical research. At present, all molecular optical imaging systems operates as stand-alone systems. It would be very powerful to integrate the operation of a molecular optical imaging system with other pre-clinical research systems to provide complementary molecular information.

SUMMARY OF THE INVENTION

The present disclosure overcomes the aforementioned drawbacks by providing an optical imaging system that can operate for efficient stand-alone applications, and can also be docked robotically on-board another imaging or irradiation instrument for combined operation.

In accordance with the present disclosure, the optical system for interfacing with a separate examination apparatus can include an imaging housing, a subject support mount, a cart, an optical arrangement, and a detection optical path. The image housing can include a housing enclosure and a housing receptor plate. The housing enclosure and housing receptor plate can be detachable from one another. Engaging the housing receptor plate with the housing enclosure can form an imaging compartment and substantially prevents light from entering the imaging compartment. The subject support mount and the housing receptor plate can be adapted to be positioned within the separate examination apparatus. The subject support mount can be adapted to receive a subject on a first support surface. The subject support mount can include at least one optical port that allows optical illumination of the subject from a direction opposite the first support surface. The cart can include an extendable arm. The optical arrangement can include an optical source, a cantilever mirror system, and the housing enclosure. The detection optical path can provide optical communication between the cantilever mirror system and an optical detector. The extendable arm can have a first end affixed to the cart and a second end affixed to the optical arrangement. The extendable arm can move from a retracted position to an extended position. In the retracted position, the optical arrangement can be positioned so the separated examination apparatus performed a separate examination process on the subject when the subject support mount and the housing receptor plate are positioned in the separate examination apparatus. In the extended position, the housing enclosure can engage the housing receptor plate. The optical arrangement can provide clearance for the extendable arm to move from the retracted position to the extended position without contacting the subject support mount or the subject. The optical source can illuminate at least a portion of the subject via the optical port when the extendable arm is in the extended position. The cantilever mirror system can be movable between at least two positions to receive an emitted optical radiation signal from the subject and reproducibly direct the emitted optical radiation signal to the optical detector.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Before the present invention is described in further detail, it is to be understood that the invention is not limited to the particular embodiments described. It is also to be understood that the terminology used herein is for the purpose of describing particular embodiments only, and is not intended to be limiting. The scope of the present invention will be limited only by the claims. As used herein, the singular forms "a", "an", and "the" include plural embodiments unless the context clearly dictates otherwise.

It should be apparent to those skilled in the art that many additional modifications beside those already described are possible without departing from the inventive concepts. In interpreting this disclosure, all terms should be interpreted in the broadest possible manner consistent with the context. Variations of the term "comprising" should be interpreted as referring to elements, components, or steps in a non-exclusive manner, so the referenced elements, components, or steps may be combined with other elements, components, or steps that are not expressly referenced. Embodiments referenced as "comprising" certain elements are also contemplated as "consisting essentially of" and "consisting of" those elements.

Figure 1:
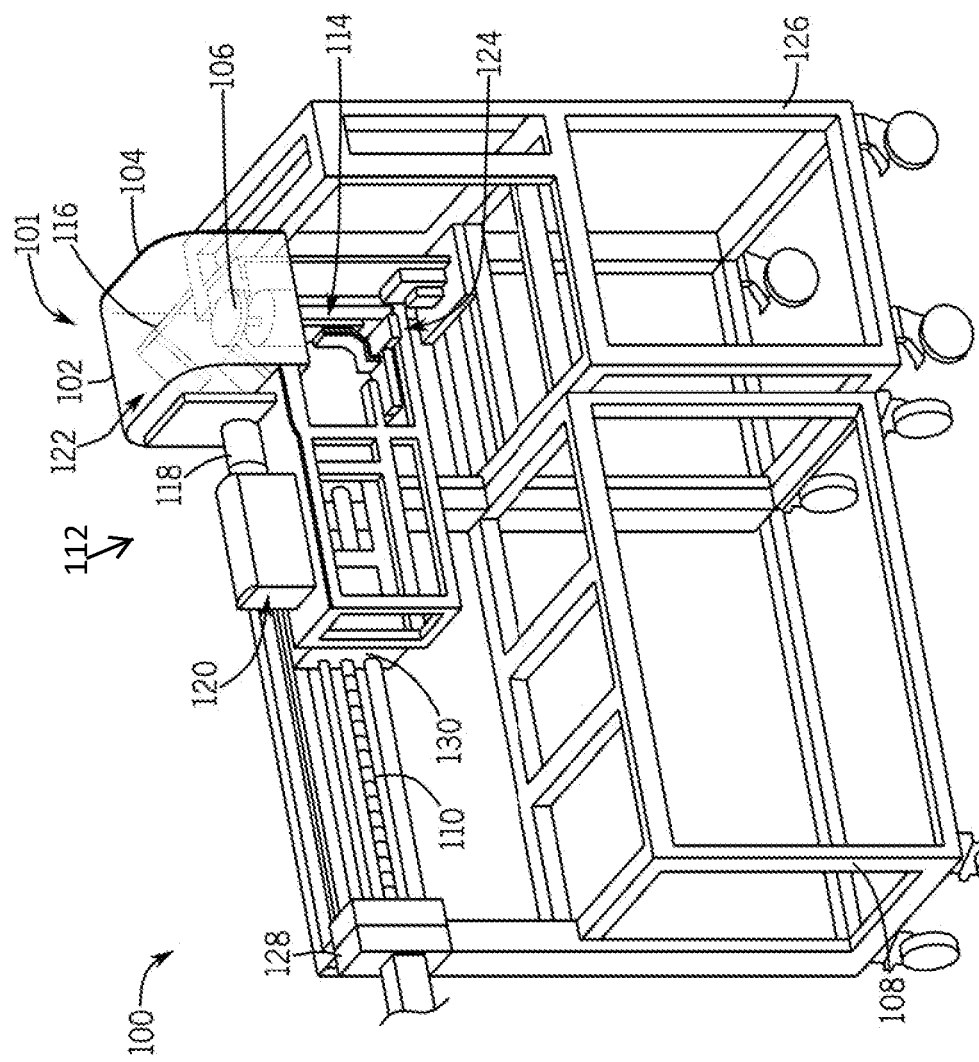
FIG. 1 shows an optical imaging system including a cart and a second cart, in accordance with the present disclosure.

Referring to FIG. 1, this disclosure provides an optical imaging system 100. The arrangement shown in FIG. 1 illustrates the optical imaging system 100 configured to operate in a standalone mode. The optical imaging system 100 can also function by interfacing with a separate examination apparatus, as described below. The optical imaging system can include one or more of the following: an imaging housing 101 including a housing enclosure 102 or a housing receptor plate 104, a subject support mount 106, the housing receptor plate 104, a cart 108 having an extendable arm 110, an optical arrangement 112 including an optical source 114, a cantilever mirror system 116, a detection optical path 118, and an optical detector 120.

In certain aspects, the cart 108 can include an extendable arm 110. In certain aspects, the cart 108 can be movable by a single person to position the optical imaging system 100 near the separate examination apparatus and remove the optical imaging 100 system from the vicinity of the separate examination apparatus.

The extendable arm 110 can include a first end 128 affixed to the cart 108 and a second end 130 affixed to the optical arrangement 112. The extendable arm 110 can move from a retracted position to an extended position and vice versa. In the retracted position, the optical arrangement 112 is positioned such that the separate examination apparatus can perform a separate examination process on the subject when the subject support mount 106 and the housing receptor plate 104 are positioned in the separate examination apparatus. In the extended position, the housing enclosure 102 can engage the housing receptor plate 104. In certain aspects, the extendable arm 110 can be a telescopic arm, a cantilever arm, a translation stage, or a combination thereof.

In certain aspects, the imaging housing 101 can include a housing enclosure 102 and a housing receptor plate 104.

The housing enclosure 102 and the housing receptor plate 104 can be detachable from one another. Engaging the housing receptor plate 104 with the housing enclosure 102 can form an imaging compartment 122 and can substantially prevent external light from entering the imaging compartment. In certain aspects, the housing receptor plate 104 can be adapted to be positioned within the separate examination apparatus.

In certain aspects, the optical arrangement 112 can include the housing enclosure 102, although the housing enclosure 102 can also be separate from the other components of the optical arrangement 112. The optical arrangement 112 can further include an optical source 114 or a cantilever mirror system 116. The optical arrangement 112 can provide clearance for the extendable arm 110 to move from the retracted position to the extended position without contacting the subject support mount 106 or the subject.

The optical source 114 can illuminate at least a portion of the subject via the optical port when the extendable arm 110 is in the extended position. The optical source 114 can be a fiber light source or a laser source. The optical source 114 can be mounted on a translation stage 124 that is coupled to the second end of the extendable arm 110. The translation stage 124 can be an x-y-z translation stage. The optical source 114 can have a substantially vertical direction of propagation.

In certain aspects, the optical imaging system 100 can include more than one optical source 114.

The cantilever mirror system 116 can be movable between at least two positions to receive an emitted optical radiation signal from the subject. The cantilever mirror system 116 can reproducibly direct emitted optical radiance from the subject to the optical detector 120. The cantilever mirror 116 system can be rotatable about an axis normal to the direction of light propagation emitted from the optical source 114. The cantilever mirror system 116 can be rotatable by 180°, 360°, or other suitable ranges of rotational motion. The cantilever mirror system 116 can include at least one mirrors, such as one, two, three, four, or more mirrors. In certain aspects, the cantilever mirror system 116 can include at least three mirrors. The cantilever mirror system 116, the at least one mirrors, or the at least three mirrors can be arranged to direct light from the subject to the optical detector 120.

Figure 2:
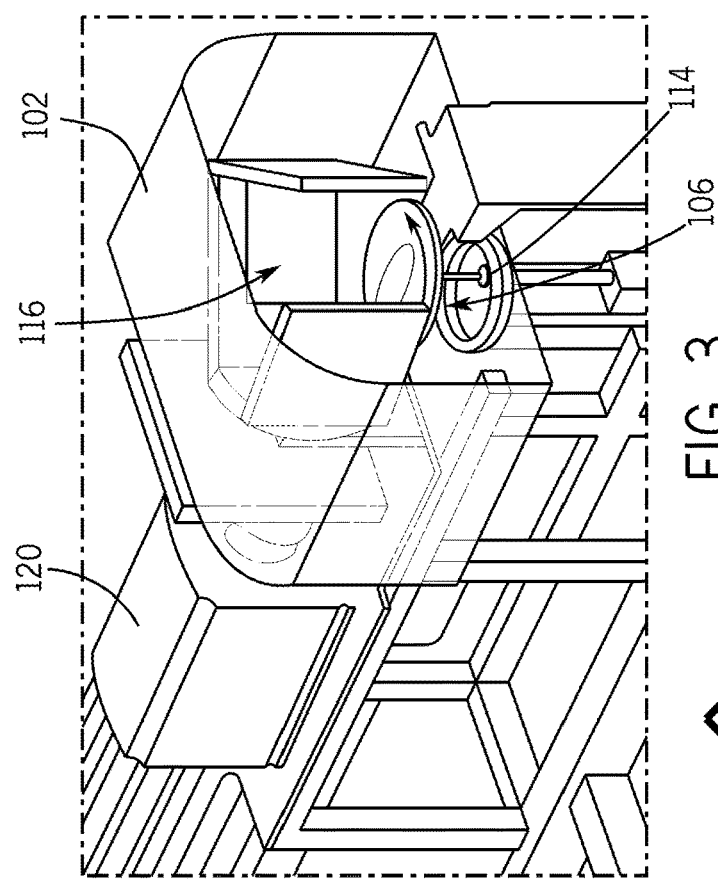
FIG. 2 shows a cantilever mirror system in a position to capture a vertical image.
Figure 3:
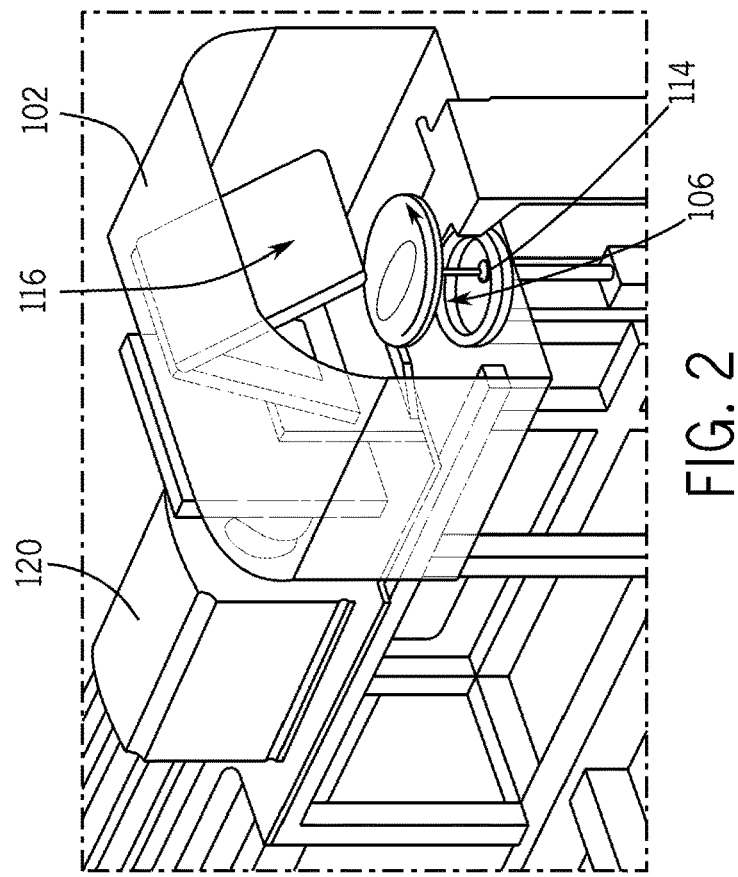
FIG. 3 shows a cantilever mirror system in a position to capture a lateral image.
Figure 4:
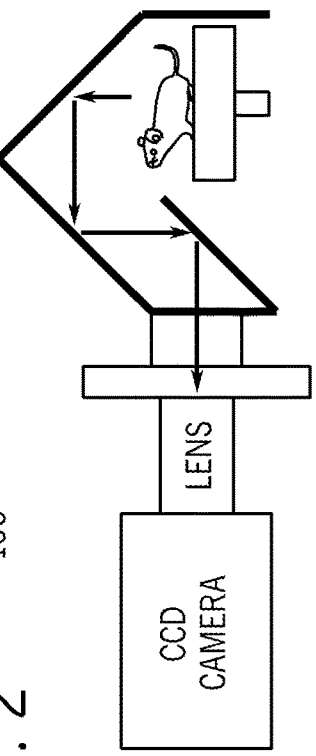
FIG. 4 is a schematic illustrating an optical path from a subject to an optical detector.

Referring to FIG. 2, the optical imaging system 100 is shown with the cantilever mirror system 116 in a vertical orientation to acquire an image from the top of the subject or from a direction substantially opposite of optical excitation. Referring to FIG. 3, the optical imaging system 100 is shown with the cantilever mirror system 116 in a lateral orientation to acquire an image from the side of the subject or from a direction substantially normal to the direction of optical excitation propagation. FIG. 4 shows a schematic representation of the path that emitted light takes from the subject, reflecting off the mirrors of the cantilever mirror system 116, and traveling to the optical detector 120.

In certain aspects, a different optical arrangement can take the place of the cantilever mirror system 116. A person having ordinary skill in the art will appreciate that a multitude of optical arrangements can achieve the same or substantially similar effect as the cantilever mirror system 116. For example, a suitable replacement for the cantilever mirror system 116 is a mirror gantry or mirror gantries, such as those described in U.S. Patent Application Pub. No. 2015/0012224, which is incorporated herein in its entirety by reference.

In certain aspects, the subject support mount 106 can be adapted to be positioned within the separate examination apparatus. The subject support mount 106 can be adapted to receive a subject. The subject can be received on a first support surface of the subject support mount 106. The subject support mount 106 can include at least one optical port that allows optical illumination of the subject from a direction opposite the first support surface. The first support surface can be substantially horizontal. The optical port can be an open passageway. The optical port can comprise a substantially transparent material.

In certain aspects, the optical imaging system 100 can further include an optical detector 120 and a detection optical path 118 providing optical communication between the cantilever mirror system 116 and the optical detector 120. The optical detector 120 can be a charge-coupled device (CCD) camera.

The optical imaging system 100 can further include other optics, such as lenses, filters, polarizers, and the like, that a person having ordinary skill in the art would understand to be suitable for use with a desired optical imaging method.

In certain aspects, the optical detector 120 can be affixed to rotate with the cantilever mirror system 116.

In certain aspects, the optical imaging system 100 can further include a controller in communication with the extendable arm 110, the optical source 114, the cantilever mirror system 116, the optical detector 120, or a combination thereof to acquire an optical imaging data set.

Figure 5:
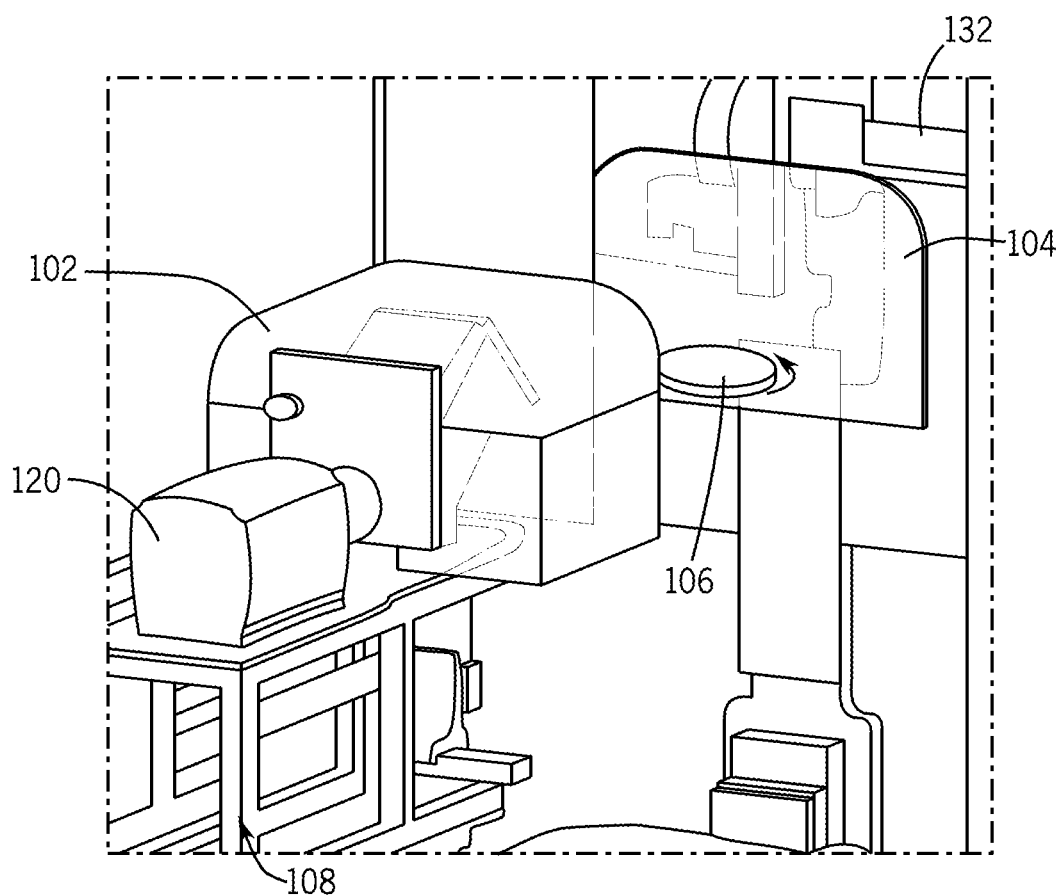
FIG. 5 shows an optical imaging system positioned near a separate examination apparatus, with an extendable arm of the optical imaging system oriented in a retracted position, so the separate examination apparatus can function in its normal mode of operation.
Figure 6:
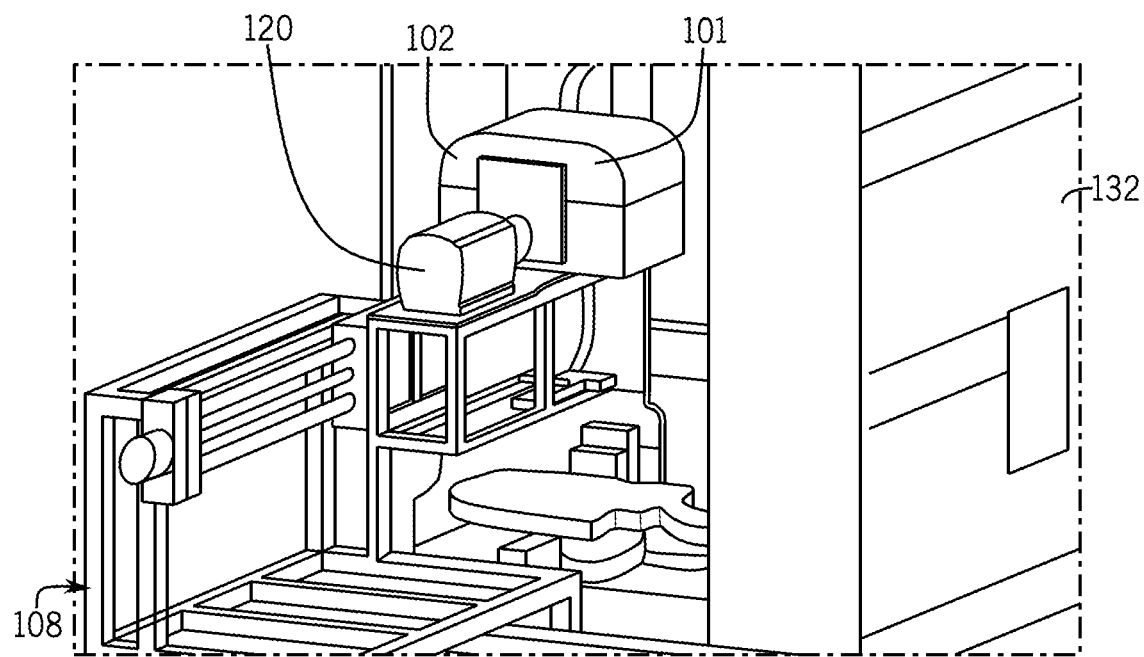
FIG. 6 shows an optical imaging system positioned near a separate examination apparatus, with an extendable arm of the optical imaging system oriented in an extended position, so the optical imaging system can perform optical imaging on a subject within the separate examination apparatus.

Referring to FIGS. 5 and 6, the optical imaging system 100 is shown in use with a separate examination apparatus 132. FIG. 5 shows the optical imaging system 100 with the extendable arm 110 in the retracted position. In the configuration shown in FIG. 5, the separate examination apparatus 132 can be used to perform the experiments that the separate examination apparatus 132 is designed to perform. FIG. 6 shows the optical imaging system 100 with the extendable arm 100 in the extended position. In the configuration shown in FIG. 6, the optical imaging system 100 can be used to perform optical imaging on the subject. It should be appreciated that moving between the retracted position and the extended position does not require the subject to be moved. It should also be appreciated that the modifications to the separate examination apparatus 132 in order to be used with the optical imaging system 100 are minor.

The separate examination apparatus 132 can include an x-ray imaging apparatus.

In certain aspects, the optical imaging system 100 can further include a second cart 126. The second cart 126 can include the subject support mount 106 and the housing receptor plate 104 for using the optical imaging system 100 in the absence of the separate examination apparatus.

In certain aspects, the subject can be an animal. In certain aspects, the subject can be a mammal. In certain aspects, the subject can be a rodent, such as a mouse.

This disclosure also provides a method of acquiring an optical imaging data set. The method can include one or more of the following: positioning the optical imaging system 100 described herein near a separate examination apparatus; extending the extendable arm 110 to engage the housing receptor plate 104 and the housing enclosure 102; and acquiring an optical imaging data set using the optical source 114, the cantilever mirror 116, and the optical detector 120.

Example 1

In pre-clinical radiation research, it is challenging to localize soft tissue targets based on cone beam computed tomography (CBCT)-guidance. As a more effective method to localize soft tissue targets, an online bioluminescence tomography (BLT) system (i.e. optical imaging system) was developed for the small animal radiation research platform (SARRP) (i.e. separate examination apparatus). The BLT system was designed to dock onto the SARRP for image acquisition and to be detached before radiation delivery. This example demonstrates BLT-guided radiotherapy and validates targeting accuracy, based on a newly developed reconstruction algorithm.

In this embodiment, the SARRP allows 360° isocentric gantry rotation and is equipped with CBCT and robotic controlled stages for animal positioning. FIG. 6 shows the BLT system consisting of a camera-filter-mirror assembly (i.e. detection optical path) docked into the SARRP. A rotating 3-mirror system directs light emitted from the object to a stationary CCD camera and supports multi-view imaging (FIGS. 2 and 3). A light-tight dome covers the mirror and object.

The workflow of online BLT-guided irradiation is described here: (1) dock BLT system onto the SARRP, (2) acquire multispectral bioluminescence imaging (BLI), (3) detach the BLT system and acquire object CBCT, (4) process the CBCT data to generate the 3D mesh of the object, and map the multispectral BLI to the mesh surface based on the geometry calibration. The 3D distribution of the bioluminescence source is then reconstructed and the center of mass (CoM) of the reconstructed source is calculated for radiation guidance.

The diffusion approximation (DA) to the radiative transport equation is widely used to model light propagation in tissue where photon transport is dominated by scattering. In the continuous wave mode, the DA and the Robin-type boundary condition are expressed as $$\begin{cases} -\nabla \cdot D(r)\nabla \Phi(r) + \mu_a(r)\Phi(r) = S(r), r \in \Omega \\ \Phi(\xi) + 2A\hat{n} \cdot D(\xi)\nabla \Phi(\xi) = 0, \xi \in \partial\Omega \end{cases} \quad (1)$$

where $\phi(r)$ is the photon fluence rate at location r in domain $\Omega$, $D(r)=1/(3(\mu_a+\mu'_s))$ is the diffusion coefficient, $\mu_a$ and $\mu'_s$ are absorption and reduced scattering coefficients, respectively, and S(r) is the bioluminescence source distribution. $\xi$ represents the points on the imaging object boundary and coefficient A can be derived from Fresnel's law depending on the refractive index of tissue and air. $\hat{n}$ is the unit vector pointing outward normal to the boundary $\partial\Omega$.

Equation (1) can be further expressed in the form of Green's functions which link the fluence rate on the object boundary and the bioluminescence source distribution. For M measurements and N mesh nodes, the relationship can be expressed as $$\begin{bmatrix} \varphi_1 \\ \vdots \\ \varphi_M \end{bmatrix} = \begin{bmatrix} G_{1,1} & \cdots & G_{1,N} \\ \vdots & \ddots & \vdots \\ G_{M,1} & \cdots & G_{M,N} \end{bmatrix} \begin{bmatrix} s_1 \\ \vdots \\ s_N \end{bmatrix}, \quad (2)$$

where $[\varphi_1, \ldots, \varphi_M]^T$ is a vector containing the fluence rate measured at the boundary, $G_{i,j}$ is the Green's function describing the relationship between the source $s_i$ and the fluence rate at detector $\varphi_j$ on the surface, and $[s_1, \ldots, s_N]^T$ is the vector of unknown bioluminescence distribution.

Multi spectral images were acquired to improve BLT reconstruction results. Equation (2) can be rewritten as $$\begin{bmatrix} \varphi(\lambda_1) \\ \vdots \\ \varphi(\lambda_k) \end{bmatrix} = \begin{bmatrix} \eta(\lambda_1)G(\lambda_1) \\ \vdots \\ \eta(\lambda_k)G(\lambda_k) \end{bmatrix} [s], \quad (3)$$

$$\varphi = \tilde{G}s,$$

where $G(\lambda_k)$ is the Green's function, extended from Eq. (2) at wavelength $\lambda_k$ and $\eta(\lambda_k)$ is the relative spectral weight which accounts for the source emission spectrum, the transmission of individual filters and CCD quantum efficiency at different wavelengths. A modified version of the open source software NIRFAST (Delghani H, Eames ME, Yalavarthy PK et al. Near infrared optical tomography using NIRFAST: Algorithm for numerical model and image reconstruction. *Commun Numer Methods Eng* 2008;25:711-732., Jermyn M, Gadyani H, Mastanduno MA, et al Fast segmentation and high-quality three-dimensional volume mesh creation from medical images for diffuse optical tomography. *J Biomed Opt* 2013;18:86007.) was used to generate the Green's function. To avoid the reconstruction algorithm biasd by the contributions from longer wavelength due to less attenuation, the measurements $\varphi$, that is $$\begin{cases} \overline{\varphi}(\lambda_k) = \varphi(\lambda_k)/\max(\varphi(\lambda_k)) \\ \overline{G}(\lambda_k) = \tilde{G}(\lambda_k)/\max(\varphi(\lambda_k)) \end{cases}. \quad (4)$$

This disclosure's approach to reconstruct the bioluminescence source distribution s is to minimize the deviation between the computed $\bar{G}s$ and measured fluence rate $\bar{\varphi}$ at the object boundary. However, the BLT reconstruction is ill-posed and underdetermined with fewer measurements than unknowns. He et al. (He X, Liang J, Wang X, et al. Sparse reconstruction for quantitative bioluminescence tomography based on the incomplete variables truncated conjugate gradient method. *Opt Express* 2010; 18:24825-24841.) introduced the IVTCG optimization algorithm and demonstrated that this algorithm can stably solve this minimization problem with an L1 regularization term. BLT minimization is given as, $$\min_s \frac{1}{2}\|\bar{G}s - \bar{\varphi}\|_2^2 + \tau\|s\|_1, \quad (5)$$

where z is a non-negative regularization parameter, $\|\bullet\|_2^2$ denotes the square of the Euclidean norm, such as $\Sigma_i(\bar{G}s-\bar{\varphi})_i^2$, and $\|s\|_1=\Sigma_i|s_i|$ is the L1 norm of s. We employed the finite element method as the framework to numerically build the Green's function and system matrix, where the imaging object was discretized into a 3D mesh from SARRP CBCT.

To improve convergence and reduce the computation time, an iterative strategy was chosen to adaptively shrink the solution space. The initial permissible solution space is the whole mesh domain except the surface nodes. The permissible region reduction factor is defined as $\beta=(N_1/N_f)^{1/(N_{it}-1)}$, where $N_1$ is the initial number of nodes for the permissible region. In this study, $N_{it}$ (number of iterations) was set to 20 and to include all the possible solutions, $N_f$ (final number of nodes) was set to 1. The objective function $$f_i = \Sigma\|\bar{G}s^{(i)} - \bar{\varphi}\|_1, \quad (6)$$

was calculated according to the reconstructed source distribution $s^{(i)}$ at the i-th iteration. The permissible region was shrunk at each iteration by first sorting the nodes in descending order of source strength, and selecting the nodes with high average source strength per 1 mm$^3$ volume until the number of nodes is equal to $N_R/\beta$ where $N_R$ is the total number of nodes in the permissible region. The solution corresponding to the minimum of the objective function was selected.

To validate BLT targeting accuracy, a small cylindrical self-powered light source, such as Trigalight®, with high CBCT contrast was placed in a phantom and also in the abdomen of a mouse carcass. The center of mass (CoM) of the source was recovered from BLT and used to guide radiation delivery. The accuracy of the BLT-guided targeting was validated with films and compared with the CBCT-guided delivery. In vivo experiments were also conducted to demonstrate the BLT localization capability for various source geometries.

For the phantom experiments, the light source was placed in one of the holes of the phantom. A small piece of closed-cell extruded polystyrene foam, such as Styrofoam®, was inserted underneath the source to minimize the air gap between source and detector points at the phantom surface. The strongest intensity on the surface did not correspond to the true source position. The largest CoM deviation between the "true" CBCT and BLT reconstructed positions of the self-powered light source, such as Trigalight®, is in the depth direction, Z-axis, at 0.6 mm. In the X- and Y-axis, the offsets between the centers of the BLT- and CBCT-guided radiation fields are less than 0.2 mm.

For the mouse carcass experiments, the location of the strongest surface bioluminescence intensity of the carcass again did not reflect the true source position. The largest CoM deviation of 0.8 mm is in the Z-axis. The average 3D offset between the true source center and BLT reconstructed CoM from 3 independent carcass measurements is 1.0±0.6 mm. The targeting difference between the BLT and CBCT-guided irradiation is minimal in the X- and Y-axis (<0.2 mm). The largest deviation was 0.8 mm along the Z-axis, which was consistent with the reconstruction results.

For the in vivo two sources study, the planar BLI can barely separate two sources, but BLT can clearly distinguish the sources. The deviations of the BLT reconstructed CoM for source 1 and 2 are 0.8 and 0.9 mm, respectively. The homogenous optical properties were assumed in this study, which possibly contributed to the unrealistic stronger source strength of source 1, compared to the source 2.

From a subcutaneous study, the reconstructed 3D distribution lying beneath the BLI intensity on the surface as expected for subcutaneous target at shallow depth. The reconstructed bioluminescence CoM is also within the tumor as depicted by CBCT image.

The present invention has been described in terms of one or more preferred embodiments, and it should be appreciated that many equivalents, alternatives, variations, and modifications, aside from those expressly stated, are possible and within the scope of the invention.

We claim:

1. An optical imaging system for interfacing with a small animal radiation research platform (SARRP) equipped with cone-beam computed tomography, the optical imaging system comprising:
   an imaging housing comprising a housing enclosure and a housing receptor plate, the housing enclosure and housing receptor plate are detachable from one another, and engaging the housing receptor plate with the housing enclosure forms an imaging compartment and substantially prevents external light from entering the imaging compartment;
   a subject support mount and the housing receptor plate are adapted to be positioned within the SARRP, the subject support mount adapted to receive a subject on a first support surface, the subject support mount comprising at least one optical port that allows optical illumination of the subject from underneath the first support surface;
   a cart comprising an extendable arm;
   an optical arrangement comprising an optical source, a cantilever mirror system, and the housing enclosure;
   a detection optical path providing optical communication between the cantilever mirror system and an optical detector;
   the extendable arm having a first end affixed to the cart and a second end affixed to the optical arrangement, the extendable arm moving from a retracted position to an extended position, in the retracted position the optical arrangement is positioned so the SARRP performs an X-ray process on the subject when the subject support mount and the housing receptor plate are positioned in the SARRP, in the extended position the housing enclosure engages the housing receptor plate;
   wherein the optical arrangement provides clearance for the extendable arm to move from the retracted position to the extended position without contacting the subject support mount or the subject;
   the optical source illuminates at least a portion of the subject via the optical port when the extendable arm is in the extended position; and the cantilever mirror system is movable between at least two positions to receive an emitted optical radiation signal from the subject and reproducibly direct the emitted optical radiation signal to the optical detector.

2. The optical imaging system of claim 1, wherein the cart is movable by a single person to position the optical imaging system near the SARRP and remove the optical imaging system from a vicinity of the SARRP.

3. The optical imaging system of claim 1, the optical imaging system further comprising a second cart that includes the subject support mount and the housing receptor plate for using the optical imaging system in the absence of the SARRP.

4. The optical imaging system of claim 1, wherein the first support surface is substantially horizontal.

5. The optical imaging system of claim 1, wherein the optical source is a fiber light source or a laser source.

6. The optical imaging system of claim 1, wherein the optical source is mounted on a translation stage that is coupled to the second end of the extendable arm.

7. The optical imaging system of claim 6, wherein the translation stage is an x-y-z translation stage.

8. The optical imaging system of claim 1, wherein the optical source has a substantially vertical direction of propagation.

9. The optical imaging system of claim 1, wherein the extendable arm is a telescopic arm, a cantilever arm, a translation stage, or a combination thereof.

10. The optical imaging system of claim 1, wherein the optical port is an open passageway or the optical port comprises a substantially transparent material.

11. The optical imaging system of claim 1, wherein the cantilever mirror system is rotatable 360° about an axis normal to a direction of light propagation emitted from the optical source.

12. The optical imaging system of claim 1, wherein the cantilever mirror system comprises at least three mirrors, the at least three mirrors arranged to direct light from the subject to the optical detector.

13. The optical imaging system of claim 1, wherein the optical detector is a charge-coupled device camera.

14. The optical imaging system of claim 1, the optical imaging system further comprising a controller in communication with the extendable arm, the optical source, the cantilever mirror system, the optical detector, or a combination thereof to acquire an optical imaging data set.

15. A method of acquiring an optical imaging data set, the method comprising:
    positioning the optical imaging system of claim 1 near the SARRP;
    extending the extendable arm to engage the housing receptor plate and the housing enclosure; and
    acquiring an optical imaging data set using the optical source, the cantilever mirror system, and the optical detector.

* * * * *